(12) United States Patent
Sun et al.

(10) Patent No.: US 7,662,084 B2
(45) Date of Patent: Feb. 16, 2010

(54) BLOOD PUMP ACTUATOR AND A BLOOD PUMP SYSTEM THEREOF

(75) Inventors: Kyung Sun, Seoul (KR); Kyu Back Lee, Seoul (KR); Yong Doo Park, Seoul (KR); Ho Sung Son, Seoul (KR); Chang Mo Hwang, Seoul (KR); Gi Seok Jeong, Daegu (KR)

(73) Assignee: Korea University Industry and Academy Cooperation Foundation, Seoul (KR)

( * ) Notice: Subject to any disclaimer, the term of this patent is extended or adjusted under 35 U.S.C. 154(b) by 537 days.

(21) Appl. No.: 10/568,090

(22) PCT Filed: Oct. 20, 2005

(86) PCT No.: PCT/KR2005/003495

§ 371 (c)(1),
(2), (4) Date: Feb. 10, 2006

(87) PCT Pub. No.: WO2006/043785

PCT Pub. Date: Apr. 27, 2006

(65) Prior Publication Data

US 2008/0161637 A1    Jul. 3, 2008

(30) Foreign Application Priority Data

Oct. 23, 2004    (KR) ............... 10-2004-0085107

(51) Int. Cl.
*A61M 1/10* (2006.01)
(52) U.S. Cl. ........................................... 600/16
(58) Field of Classification Search .............. 600/16
See application file for complete search history.

(56) References Cited

U.S. PATENT DOCUMENTS

| | | | |
|---|---|---|---|
| 4,360,324 A | 11/1982 | Ohara et al. | |
| 4,557,726 A * | 12/1985 | Reinicke | 604/67 |
| 4,623,350 A * | 11/1986 | Lapeyre et al. | 623/3.17 |
| 4,627,419 A | 12/1986 | Hills | |
| 5,092,878 A | 3/1992 | Miyata | |
| 5,263,978 A | 11/1993 | Kaufmann et al. | |
| 5,655,893 A | 8/1997 | Kubo | |
| 5,655,953 A * | 8/1997 | Murakami et al. | 451/62 |
| 5,980,448 A | 11/1999 | Heilman et al. | |

(Continued)

FOREIGN PATENT DOCUMENTS

SU    816458 B  *  3/1981

*Primary Examiner*—Carl H Layno
*Assistant Examiner*—Jeremiah T Kimball
(74) *Attorney, Agent, or Firm*—Lucas & Mercanti, LLP (57) ABSTRACT

A blood pump actuator to generate a driving force for driving a blood pump is disclosed. The blood pump actuator includes: a motor unit having a stator and a rotor, and rotating to generate a rotating force; a cam unit to convert the rotating motion of the motor unit into a rectilinear reciprocating motion; and a bellows unit having a bellows, which is expandable and contractible and contains a fluid therein, and an upper bellows plate and a lower bellows plate respectively attached to the upper and lower ends of the bellows, wherein the lower bellows plate moves upwards and downwards in a vertical direction according to the rectilinear reciprocating motion of the cam unit engaging with the lower bellows plate, and the bellows repeatedly expands and contracts according to the vertical movement of the lower bellows plate.

20 Claims, 4 Drawing Sheets

U.S. PATENT DOCUMENTS 6,066,085 A * 5/2000 Heilman et al. ............... 600/16
6,123,726 A    9/2000 Mori et al.
7,238,171 B2 * 7/2007 Faries et al. ................. 604/118
2002/0102169 A1 8/2002 Wampler
2002/0169399 A1 11/2002 Rastegar et al.

* cited by examiner

BLOOD PUMP ACTUATOR AND A BLOOD PUMP SYSTEM THEREOF

This patent application claims the benefit of priority from Korean Patent Application No. 10-2004-0085107 filed Oct. 23, 2004 through PCT Application Serial No. PCT/KR2005/003495 filed Oct. 20, 2005 the contents of which are incorporated herein by reference.

TECHNICAL FIELD

The present invention relates, in general, to blood pump actuators and blood pump systems having the actuators and, more particularly, to a blood pump actuator which has a small and light structure and is able to convert an inlet rotating motion into a rectilinear reciprocating motion and to a blood pump system having the actuator.

BACKGROUND ART

An artificial heart may be used for a heart patient if a surgeon determines that the actual heart of the patient cannot operate normally and thereby cannot maintain the blood pumping function. Conventional artificial hearts are classified into two types, which are total artificial hearts (TAH) and ventricular assist devices (VAD), according to the original intended function of the heart and the actual function of the heart in the body of a patient. The TAH is implanted in the body of a patient after the human heart has been removed from the body, so that the TAH must execute the heart's function in place of the removed human heart. However, the VAD is implanted in the body of a patient without removing the human heart from the body, and assists the function of the left or right ventricle.

Conventional VADs are classified into two types, which are intracorporeal VADs and extracorporeal VADs, according to the location of a VAD relative to the body of a patient. Because the TAH completely replaces the human heart of a patient, that is, occupies the physical space and provides the entire functionality of the human heart, the TAH requires a donor, thereby causing several problems. However, the VAD, which is used in conjunction with the human heart without removing the human heart from a patient, comprises an artificial blood pump connected to the ventricles of the human heart and to the artery of the patient through blood conduits, thus feeding blood from an inlet to an outlet of the pump to discharge the blood to the artery. Unlike the TAHs, the VADs replace only some of the functionality of the human heart.

The VAD uses an artificial blood pump to assist the blood pumping function of the human heart to efficiently pump the blood required by the body of a patient as long as some of the functionality of the human heart is maintained. When surgeons determine that the functioning of the human heart of the patient using the artificial blood pump of the VAD has improved and the human heart can execute its normal functions, the blood pump of the VAD may be disconnected from the patient so that the patient may live normally.

The blood pumps are classified into a pulsatile blood pump and a non-pulsatile blood pump according to the blood current generation manner of the blood pump. The pulsatile blood pump is configured such that, when a blood bag or a blood containing part functioning as an artificial ventricle is compressed, the pump discharges blood under pressure. The non-pulsatile blood pump is configured such that an impeller, which is in direct contact with blood, is rotated at a high speed and generates a rotating force to pump blood out.

The conventional pulsatile blood pump is used with a pump actuating device to cause variation in pressure in an artificial ventricle. The conventional actuating devices for pulsatile blood pumps are classified into a pneumatic device to compress a blood sac or diaphragm using compressed air and a mechanical device to mechanically compress a blood sac or diaphragm using a mechanical mechanism. The pneumatic actuating device for pulsatile blood pumps connects compressed air, prepared in a hospital, compresses a blood bag of the pump using the compressed air and restores the blood bag using a vacuum. Furthermore, a mobile actuating device for pulsatile blood pumps, which has both a vacuum pump and an air compressor and is connected to an artificial ventricle, has been proposed and used. However, the conventional mobile actuating device having a vacuum pump and an air compressor is problematic in that the device has a large size and a heavy weight so that the device is not easy to use in a place other than hospitals, thus restricting the movement of a patient.

DISCLOSURE

Technical Problem

Accordingly, the present invention has been made keeping in mind the above problems occurring in the prior art, and an object of the present invention is to provide a blood pump actuator which has a small, light and rigid structure, and to provide a blood pump system having the actuator.

Technical Solution

In order to accomplish the above object, an embodiment of the present invention provides a blood pump actuator to generate a driving force for driving a blood pump, the actuator comprising:

a motor unit having a stator and a rotor, and rotating to generate a rotating force;

a cam unit to convert the rotating motion of the motor unit into a rectilinear reciprocating motion; and a bellows unit comprising a bellows, which is expandable and contractible and contains a fluid therein, and an upper bellows plate and a lower bellows plate respectively attached to the upper and lower ends of the bellows, wherein the lower bellows plate moves upwards and downwards in a vertical direction according to the rectilinear reciprocating motion of the cam unit engaging with the lower bellows plate, and the bellows repeatedly expands and contracts according to the vertical movement of the lower bellows plate.

In the blood pump actuator of the present invention, the cam unit may comprise:

a cam having a cam guide continuously formed around the outer circumferential surface of a cylindrical body, and a cam cover mounted to the upper end of the cam; and a cam gear mounted to an end of the cam cover such that the cam gear is concentric with the cam and receives the rotating force of the motor unit.

In the blood pump actuator according to the present invention, the bellows unit may be placed on the upper end of the cam unit. The lower bellows plate may include a lower bellows plate extension part which extends, at an edge of the lower bellows plate, towards the cam unit, is perpendicular to the lower bellows plate, is spaced apart from the cam unit, and is placed outside the cam unit. The lower bellows plate extension part may include a cam guide engagement part on the inner surface thereof to engage with the cam guide.

In the blood pump actuator according to the present invention, the cam guide may be a protruding cam guide, while the cam guide engagement part may be a depressed cam guide engagement part.

In the blood pump actuator according to the present invention, the cam guide may be a depressed cam guide, while the cam guide engagement part may be a protruding cam guide engagement part.

In the blood pump actuator according to the present invention, the cam guide may have the shape of a sine curve.

In the blood pump actuator according to the present invention, the cam guide may have the shape of an asymmetrical curve.

In the blood pump actuator according to the present invention, the cam guide may have a stepped shape.

In the blood pump actuator according to the present invention, the cam guide may have the shape of a linear function curve having a peak and a trough.

In the blood pump actuator according to the present invention, the lower bellows plate extension part may be. continuously formed around the outer circumferential surface of the lower bellows plate.

In the blood pump actuator according to the present invention, the lower bellows plate extension part may be discontinuously formed around the outer circumferential surface of the lower bellows plate.

In the blood pump actuator according to the present invention, the lower bellows plate may include two or more discontinuous lower bellows plate extension parts which are arranged at respective positions dividing the lower bellows plate into even sectors.

In the blood pump actuator according to the present invention, the motor unit may have a housing at a lower part thereof and may be placed below the bellows unit, with a bellows guide extension part provided on an edge of the lower bellows plate and extending toward the cam unit, while the housing of the motor unit may be provided with a bellows guide to guide the bellows guide extension part.

In the blood pump actuator according to the present invention, the bellows guide extension part may be a rod-shaped part, while the bellows guide may be a linear bushing to receive the bellows guide extension part therein.

The blood pump actuator according to the present invention may further include a reduction gear mechanism placed between the motor unit and the cam unit.

In the blood pump actuator according to the present invention, the reduction gear mechanism may comprise a planetary gear mechanism.

In the blood pump actuator according to the present invention, the planetary gear mechanism may comprise a sun gear having a gear part around the outer circumferential surface thereof, a carrier placed at a predetermined height different from the height of the gear part of the sun gear, at least two or more planetary gears mounted on the surface of the carrier and engaging with the gear part of the sun gear, and a ring gear having a gear part around the inner circumferential surface thereof and engaging with the planetary gears. The carrier may be mounted to the inner surface of the rotor, the sun gear may be concentric with the cam unit, and the ring gear may be integrally formed with the cam gear.

The blood pump actuator according to the present invention may further comprise a pressure regulating unit to regulate pressure in the bellows.

In the blood pump actuator according to the present invention, the pressure regulating unit may comprise:

a pressure gauge connected to the bellows through a pressure connection part and measuring the pressure of the fluid in the bellows;

a fluid pump connected to the pressure connection part and supplying or discharging the fluid to or from the bellows;

control valves respectively placed between the bellows and the pressure gauge and between the pressure gauge and the fluid pump and controlling the flow of the fluid; and a pressure control unit to control both the control valves and the fluid pump in response to pressure in the bellows measured by the pressure gauge, thus maintaining the inner pressure of the bellows within a predetermined pressure range.

In accordance with another aspect, the present invention provides a blood pump system comprising: the blood pump actuator, and a diaphragm which communicates with the bellows of the blood pump actuator through a connection part and is deformed according to changes in volume of the bellows, thus pumping blood from the system to a desired place in the body of a patient according to the deformation of the diaphragm.

ADVANTAGEOUS EFFECTS

The present invention having the above-mentioned construction provides the following advantages.

First, the present invention provides a blood pump actuator and a blood pump system, which may used as pulsatile VADs to remove the requirements for large capacity vacuum pumps and peripheral devices thereof from the VADs, thus accomplishing the recent trend of smallness, lightness and portability of the VADs, and has a hygienic structure that isolates a blood containing part from a blood pump actuating part, thus improving the hygiene of the VADs.

Second, the present invention provides a blood pump actuator and a blood pump system, which has a simple cam unit and minimizes the frictional surface area of the cam unit, thus having increased durability.

MODE FOR INVENTION

Herein below, a preferred embodiment of the present invention will be described in detail with reference to the accompanying drawings.

Figure 1:
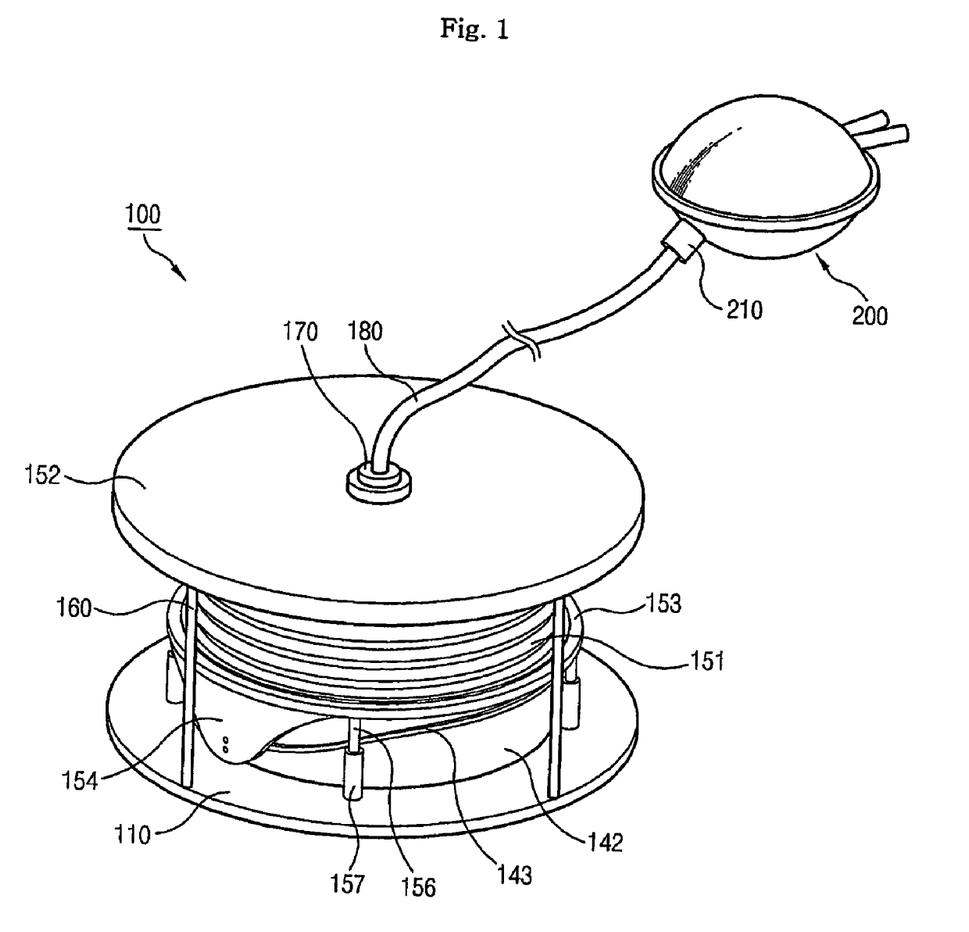
FIG. 1 is a perspective view illustrating a blood pump actuator according to an embodiment of the present invention and a blood pump system having the actuator.
Figure 2:
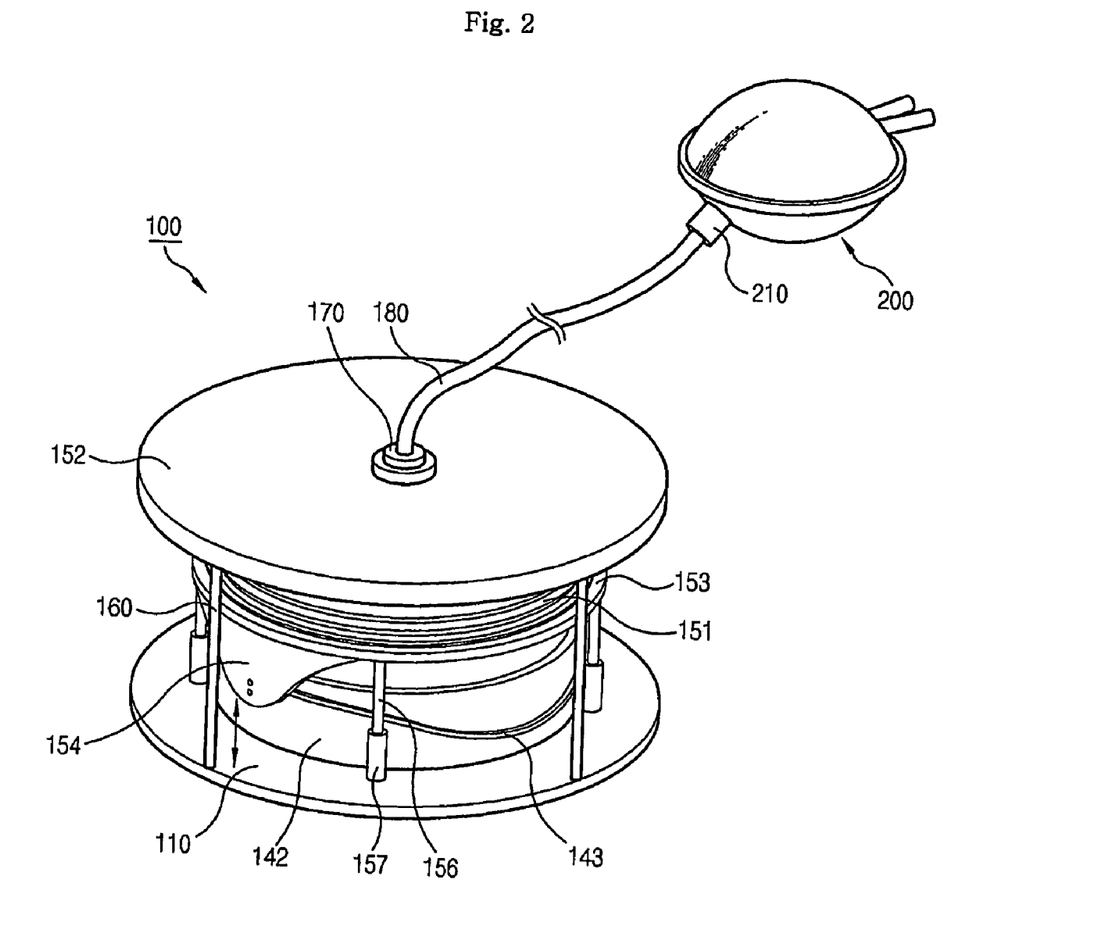
FIG. 2 is a perspective view schematically illustrating the operation of the embodiment of FIG. 1.
Figure 3:
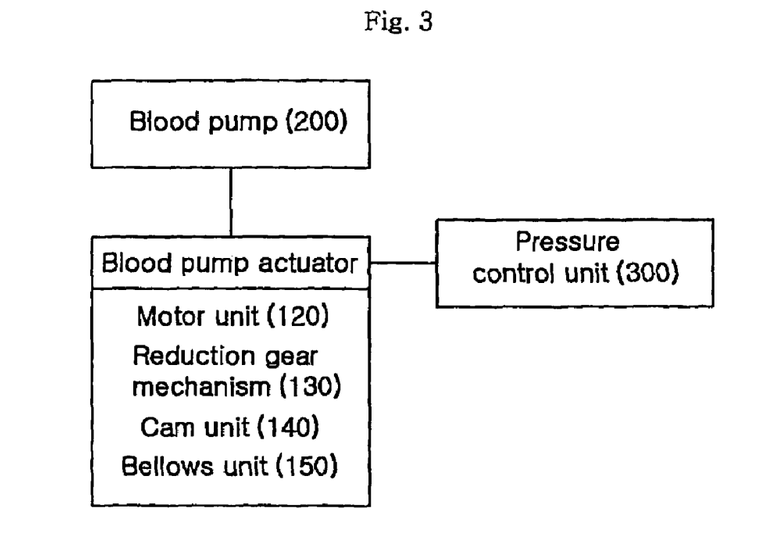
FIG. 3 is a block diagram schematically illustrating the construction of the blood pump system according to the present invention.
Figure 4:
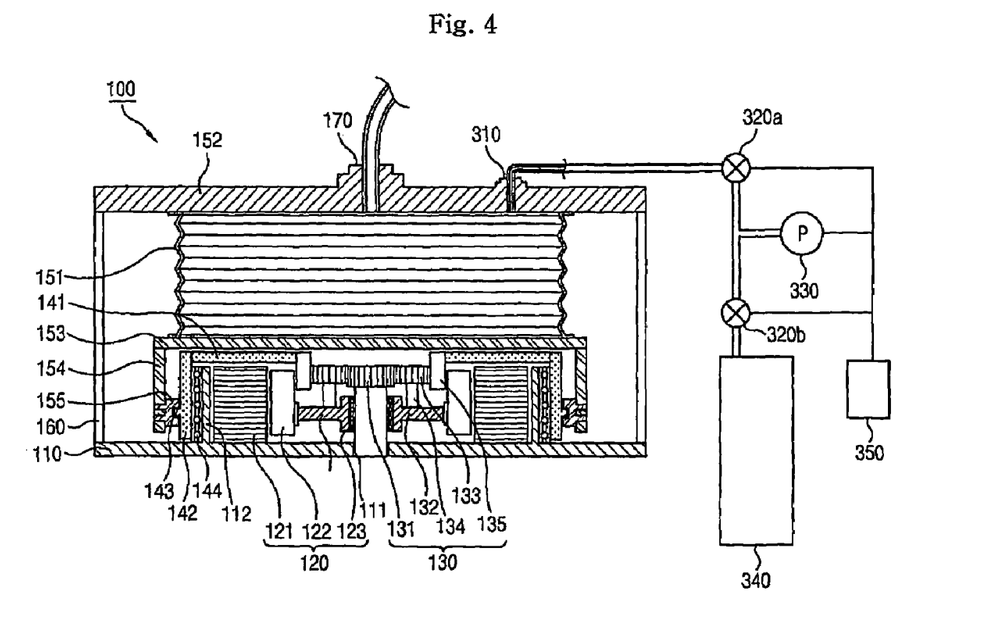
FIG. 4 is a sectional view illustrating the blood pump actuator according to the embodiment of the present invention.

FIGS. 1 and 2 are perspective views illustrating the construction and operation of a blood pump actuator according to an embodiment of the present invention and a blood pump system having the actuator (in this drawing, a pressure control unit is not shown). FIG. 3 is a block diagram schematically illustrating the construction of the blood pump system according to the present invention. FIG. 4 is a sectional view illustrating the blood pump actuator according to the embodiment of the present invention.

The blood pump actuator 100 according to the present invention includes a motor unit 120, a cam unit 140 and a bellows unit 150 (see FIG. 3). As shown in FIG. 3, the motor unit 120 executes a rotating motion to generate a rotating force, and transmits the rotating force to the cam unit 140. The cam unit 140 converts the rotating motion, transmitted from the motor unit 120, into a rectilinear reciprocating motion, thus vertically expanding and contracting the bellows unit 150 connected to the cam unit 140, and transmitting a driving force to feed blood to a blood pump 200.

The motor unit 120 includes a stator 121, a rotor 122 and a power supply unit (not shown) which are placed in a housing 110. Electric power is supplied both to the stator 121 and to the rotor 122 by means of the power supply unit, so that an electromagnetic force is generated between the stator 121 and the rotor 122 and rotates the rotor 122, thereby generating a rotating force. The operation of the motor unit 120 is controlled by a motor control unit (not shown). In the above state, the motor control unit controls the operation of the motor unit 120 in response to input signals, such as a preset voltage and electric power.

In the embodiment of FIGS. 1 and 4, the motor unit 120 is placed below the bellows unit 150. However, it should be understood that this location of the motor unit 120 relative to the bellows unit 150 does not limit the construction of the present invention. Furthermore, the motor of the motor unit 120 may be selected from a variety of conventional motors, such as a DC motor or a brushless DC motor (BLDC motor).

The rotating force, generated by the motor unit 120, is transmitted to the cam unit 140. The cam unit 140 comprises a cam 142, a cam cover 141, a cam guide 143 and a cam gear 135. As shown in FIGS. 1 and 4, the cam 142 is a cylindrical cam which is concentric with the central axis of the motor unit 120. In the present invention, it is not necessary to dispose the cam unit 140 to be concentric with the motor unit 120. However, to accomplish the recent trend of smallness, compactness and lightness of the blood pump actuator through optimal design of the actuator, the cam unit 140 is preferably concentric with the motor unit 120.

The cam cover 141 having a disc shape is mounted to the upper end of the cam 142, so that the cam cover 141 protects the motor unit 120 placed below the cam cover 141. The cam gear 135 is provided along the inner edge of the disc-shaped cam cover 141 and extends downwards toward the motor unit 120 placed below the cover 141. The cam gear 135 receives the rotating force from the motor unit 120. As shown in FIG. 4, the cam gear 135 comprises an internal gear which engages with a reduction gear mechanism 130. The internal gear structure of the cam gear 135 is an embodiment of the present invention, however, it should be understood that the structure of the cam gear 135 may be altered without affecting the functionality of the present invention.

The cam guide 143 in a wavy shape having a peak and a trough is formed around the outer circumferential surface of the cylindrical body of the cam 142. The cam guide 143 may have the shape of a sine curve as shown in FIG. 1, or may have a stepped shape, or the shape of a linear function curve having a peak and a trough. The cam guide 143 may have a variety of shapes according to the operational conditions under which the blood pump actuator is to be used, for example, the cam guide 143 may have a wavy shape of an asymmetrical curve.

Furthermore, a partition wall 112 is placed between the inner surface of the cam 142 and the motor unit 120, thus reliably protecting the motor unit 120. A cam bearing 144 is provided between the inner surface of the cam 142 and the partition wall 112, thus allowing the cam 142 to smoothly rotate without frictional interference.

The bellows unit 150 is provided on the upper end of the cam unit 140 and comprises an upper bellows plate 152, a lower bellows plate 153 and a bellows 151 which is placed between the upper bellows plate 152 and the lower bellows plate 153.

The bellows 151 of the present invention is preferably made of metal or high polymer. However, the bellows 151 may be made of a variety of materials without being limited to the above-mentioned materials as long as the material of the bellows is freely flexible to restore its original shape and has high pressure resistance and high durability. Furthermore, the bellows 151 contains therein a compressible or incompressible fluid, which is a gas or a liquid.

a lower bellows plate extension part 154 extends downwards from an edge of the upper bellows plate 152 toward the cam unit 140 which is placed below the lower bellows plate 153. The lower bellows plate extension part 154 extends toward the cam unit 140 and is placed outside the cam unit 140, as shown in FIGS. 1 and 4. A cam guide engagement part 155 is provided on the lower bellows plate extension part 154. The cam guide engagement part 155 is mounted to the inner surface of the lower bellows plate extension part 154, extends toward the cam unit 140, and engages with the cam guide 143 formed around the outer circumferential surface of the cam 142. In the embodiment of the present invention, the cam guide 143 is a protruding cam guide, while the cam guide engagement part 155 is a depressed cam guide engagement part. However, the shape of the cam guide 143 and the cam guide engagement part 155 may be variously altered without affecting the functionality of the present invention. For example, the cam guide 143 may be a depressed cam guide, while the cam guide engagement part 155 may be a protruding cam guide engagement part.

Furthermore, the lower bellows plate extension part 154 may be configured as an extension part which is discontinuously formed around the outer circumferential surface of the lower. bellows plate 153 as shown in FIG. 1. Alternatively, the lower bellows plate extension part 154 may be configured as an extension part which is continuously formed around the outer circumferential surface of the lower bellows plate 153, although the continuous extension part is not shown in the accompanying drawings. When the lower bellows plate extension part is a continuous extension part, a plurality of cam guide engagement parts may be provided in the cam unit 140. Furthermore, two or more lower bellows plate extension parts 154 may be provided on the lower bellows plate 153 as shown in FIG. 4. In the above state, the two or more lower bellows plate extension parts 154 are preferably arranged on the outer circumferential edge of the lower bellows plate 153 at positions dividing the lower bellows plate 153 into even sectors in an effort to avoid eccentricity or imbalance of the lower bellows plate 153.

To more reliably prevent eccentricity or imbalance of the lower bellows plate, a plurality of bellows guide extension parts 156 may extend downwards from the lower bellows plate 153 toward the cam unit 140, while a plurality of bellows guides 157 may be provided on the housing 110 of the motor unit 140 to guide movement of the bellows guide extension parts 156. To simplify the construction of the actuator, each of the bellows guide extension part 156 preferably has a rod shape, while each of the bellows guides 157 is preferably configured as a linear bushing to receive the rod-shaped bellows guide extension part 156 therein. However, the shape of the bellows guide extension part and the bellows guide is not limited to the above-mentioned shape, but may be variously constructed if the construction of the present invention does not cause interference with the lower bellows plate extension part 154.

The power transmission between the motor unit 120 and the cam unit 140 may be accomplished using a direct transmission mechanism or an indirect transmission mechanism which is a reduction gear mechanism using an intermediate medium to control the relationship between the speed and torque of a rotating motion while transmitting the rotating force. The reduction gear mechanism of the present invention preferably comprises a worm gear mechanism. However, a planetary gear mechanism 130 is most preferably used as the reduction gear mechanism because the planetary gear mechanism can execute the function of desired speed reduction in a limited space and can vary the reduction ratio.

Figure 5:
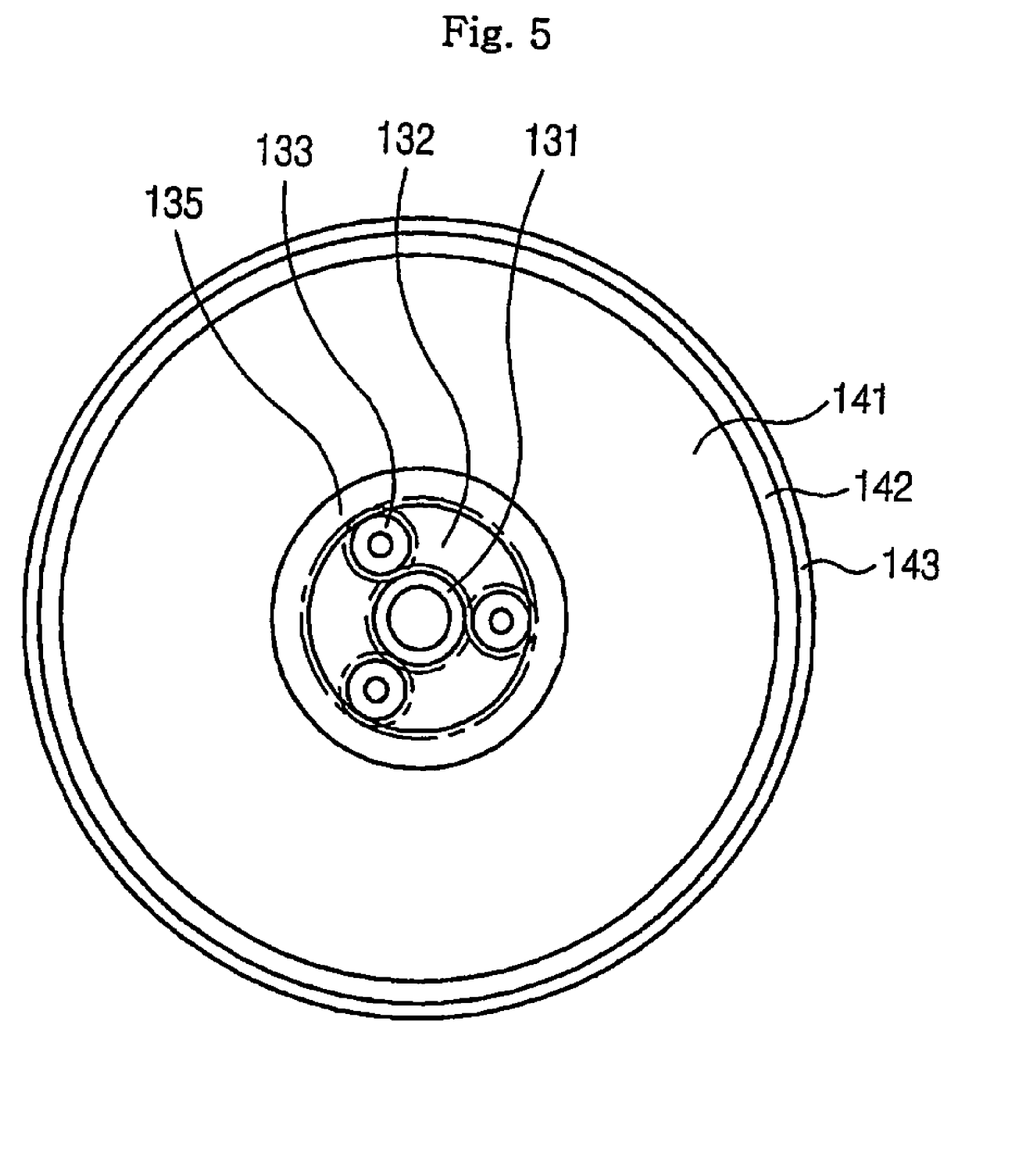
FIG. 5 is a plan view schematically illustrating the construction of a planetary gear mechanism which is used as the reduction gear mechanism of the blood pump actuator according to the embodiment of the present invention.

FIG. 4 is a sectional view illustrating the blood pump actuator having the planetary gear mechanism 130. FIG. 5 is a plan view schematically showing the structure including the planetary gear mechanism 130 and the cam unit 140. The planetary gear mechanism 130 comprises a sun gear 131, a carrier 132, one or more planetary gears 133, and a ring gear 135. The sun gear 131 serves as a central shaft of the planetary gear mechanism. In the embodiment of the present invention of FIGS. 4 and 5, the planetary gear mechanism 130 is used as the reduction gear mechanism, in which the cam gear 135 acts as the ring gear 135 of the planetary gear mechanism 130.

A through hole 111 is formed through the center of the lower plate of the housing 110 of the motor unit 140, so that the sun gear 131, acting as the central shaft of the planetary gear mechanism 130, is held in the through hole 111. The sun gear 131 is concentric with the cam unit 140 and is externally threaded around the outer circumferential surface thereof to form a gear part. The carrier 132 extends inwards in radial directions from the inner surface of the rotor 122 of the motor unit 120 towards the sun gear 131 acting as the central shaft. The carrier 132 may be a disc plate having a center through hole. In the present invention, to accomplish reliable operation of the planetary gear mechanism 130, a rotor bearing 123 is preferably provided between the carrier 132 and the outer circumferential surface of the sun gear 131. One or more planetary gears 133 are placed on one surface of the carrier 132. The planetary gears 133 are rotatably supported by respective planetary gear shafts 134, which are provided on the upper surface of the carrier 132, and externally engage with the gear part of the sun gear 131. The ring gear 135 is concentric with both the sun gear 131 and the carrier 132, and is internally threaded to form a gear part internally engaging with the planetary gears 133. As described above with reference to FIG. 4, the cam gear 135 is used as the ring gear 135 of the planetary gear mechanism 130. However, the ring gear may be produced separately from the cam gear and assembled in the planetary gear mechanism without affecting the functionality of the present invention.

The planetary gear mechanism 130 is operated as follows. When the rotor 122 of the motor unit 120 is rotated with the sun gear 131 in a fixed and immobile state, the carrier 132 connected to the rotor 122 is rotated. If the carrier 132 is rotated, the planetary gears 133, which are rotatably coupled to the planetary gear shaft 134 provided on the upper surface of the carrier 132, revolve around the outer circumferential surface of the sun gear 131 and, at the same time, rotate around their axes. Due to the rotating motion of the planetary gears 133, the cam gear 135, which serves as a ring gear internally engaging with the planetary gears 133, is rotated.

Thus, the rotating motion of the rotor 122 is finally output as rotating motion of the cam gear 135. In the above state, the speed of the output rotating motion of the cam gear 135 has been reduced. However, the operation of the present invention is not limited to the above-mentioned operation to reduce the speed, but may provide a variety of rotational speeds by controlling the rotation of the sun gear 131. Described in detail, if the operational conditions of the sun gear 131, acting as the central shaft of the reduction gear mechanism, are appropriately preset according to the desired operation of the reduction gear mechanism, for example, if the sun gear is preset to execute free rotation, forward rotation or reverse rotation, and, furthermore, the planetary gears 133 are not fixed, but rotate to thereby transmit the rotating force to the cam gear 135, it is possible to appropriately control the forward and reverse rotation of the sun gear 131 and variation in rotational speed of the sun gear 131, thus controlling the speed and torque of the cam gear 135 acting as an output shaft, and finally controlling the speed and torque of the bellows while the bellows vertically expands and contracts.

The vertical expanding and contracting motion of the blood pump actuator 100 according to the present invention is transmitted to the blood pump 200 by way of the bellows unit 150. In the above state, to stably fix the upper bellows plate 152 without allowing it to move even if the lower bellows plate 153 executes a rectilinear reciprocating motion, a plurality of bellows unit support columns 160 connects the upper bellows plate 152 to the housing 110 of the motor unit 120. In the present invention, the bellows unit support columns 160 may have a rod shape as shown in FIG. 1, however, the shape of the bellows unit support columns 160 is not limited to the rod shape.

Furthermore, the upper bellows plate 152 of the bellows unit 150 is provided with a connection part 170, so that a connection tube 180 to feed blood is connected to the blood pump 200 at the connection part 170. Thus, due to the repeated vertical expanding and contracting motion of the bellows unit 150, fluid contained in the bellows 152, which is a gas or a liquid, is fed to the blood pump 200 through the connection part 170 and the connection tube 180. The construction of the blood pump 200 is not shown in detail in the drawings, but it should be understood that the blood pump 200 may be a conventional blood pump which has been typically used in the related art.

Furthermore, the blood pump actuator according to the present invention may further comprise a pressure control unit 300 to secure reliable and continuous operation of the blood pump actuator 100. As shown in FIG. 4, the pressure control unit 300 is connected to the actuator 100 through a pressure connection part 310 provided on a predetermined portion of the bellows unit 150. The pressure control unit 300 comprises a pressure gauge 330, which is a pressure sensor to sense pressure in the bellows unit 150, a fluid pump 340 to feed fluid into the bellows unit 150, and two control valves 320*a* and 320*b* mounted on a line between the fluid pump 340 and the bellows unit 150. The pressure control unit 300 further comprises a pressure control unit 350, which is connected both to the pressure gauge 330 and to the two control valves 320*a* and 320*b*, and outputs control signals to the two control valves 320*a* and 320*b*.

When the pressure gauge 330 senses that the pressure in the bellows unit 150 exceeds a preset reference pressure range or does not reach the preset reference pressure range, the pressure control unit 300 controls the operation of the fluid pump 340 to feed or discharge fluid, thus maintaining the pressure in the bellows unit 150 within the appropriate range. If the pressure control unit 300 is used, the control valve 320*a* is opened, so that the rotating direction of the fluid pump 340 and the opening/closing operation of the control valve 320b are controlled by the pressure control unit 350, thus causing the bellows unit 150 to maintain an appropriate inner pressure.

When pressure, exceeding the preset reference pressure range, is present in the bellows unit 150, the blood pump unit 200 has reduced life span expectation and system efficiency. On the contrary, when pressure that does not reach the preset reference pressure range acts in the bellows unit 150, a suction force acts in a conduit part (around a sutured part of a patient), at which the blood pump is connected to the patient, so that air may be introduced into blood and may inflict a mortal wound on the patient. Thus, due to the pressure control unit 300 which is used with the blood pump actuator 100 of the present invention, the actuator 100 can be free from malfunctions caused by variation in pressure in the bellows unit 150 during operation of the actuator to generate a driving force required by the blood pump 200. Thus, the actuator 100 can more reliably supply the driving force to the. blood pump 200.

Herein below, the operation of the blood pump actuator having the above-mentioned construction according to the embodiment of the present invention will be described.

When a control signal, which is equal to the preset reference voltage signal, is output from the motor unit control unit (not shown) to the motor unit, the rotor 122 is rotated by electromagnetic action between the stator 121 and the rotor 122. Thus, the carrier 132, which extends from the rotor 122, is rotated, so that the sun gear 131 and the planetary gears 133 can be rotated at appropriate speeds and with appropriate torques corresponding to the speeds due to the relative rotating motion between them and, finally, the rotating motion of the rotor 122 is transmitted to the cam gear 135 acting as a ring gear, which is an output gear engaging with and rotating together with the external gear parts of the planetary gears, after the speed of the rotating force has been changed to an appropriate speed. Thus, both the cam cover 141 and the cam 141, which are connected to the cam gear 135, are rotated along with the cam gear 135.

The cam guide 143, which is formed around the outer circumferential surface of the cam 141 and has a peak and a trough, engages with the cam guide engagement part 155 provided on the lower bellows plate extension part 154, so that the rotating motion of the cam 141 is converted into the vertical reciprocating motion of the lower bellows plate 153. FIG. 1 shows the lower bellows plate 153 which has been placed at a lower position thereof, while FIG. 2 shows the lower bellows plate 153 which has been shifted to an upper position thereof due to a rotating motion of the cam 141.

Because the lower bellows plate 153 executes a vertical reciprocating motion, the bellows 151, integrated with the lower bellows plate 153, repeatedly expands and contracts. When the bellows 151 repeatedly expands and contracts and changes the volume thereof, the fluid contained in the bellows 151 is fed to the blood pump 200 through the connection part 170, which is formed on the upper bellows plate 152, and the connection tube 180 extending from the connection part 170 to the pump 200. During the above-mentioned operation, pressure in the bellows 151 is appropriately controlled by the pressure control unit 300 and is maintained at a predetermined pressure.

The fluid, which has been fed into the blood pump 200 through the blood pump connection part 210 connected to the connection tube 180, is introduced into an actuating part (not shown) of the pump 200, which is isolated from a blood containing part containing blood therein, thus increasing or reducing the pressure in the actuating part of the pump 200.

Variation in pressure in the actuating part of the pump 200 causes variation in pressure in the blood containing part of the pump 200, thus causing the blood containing part to pump blood out. A flexible diaphragm is placed in the blood pump 200 at a position, at which the blood containing part is isolated from the actuating part, thus efficiently coping with variations in pressure. Thus, when the bellows 151 contracts or when the lower bellows plate 153 is moved upwards, pressure in the actuating part of the blood pump 200 increases and causes the blood containing part to pump blood out to desired places in the body of the patient. However, when the bellows 151 expands or when the lower bellows plate 153 is moved downwards, pressure in the actuating part of the blood pump 200 decreases so that the actuating part contracts. In the blood pump 200, a unidirectional valve, such as a check valve (not shown), is preferably provided in the blood outlet of the blood containing part of the pump 200, thereby preventing blood from flowing into the blood containing part backward.

In the above-mentioned embodiments, the blood pump actuator basically comprises a motor unit, a cam unit and a bellows unit, and selectively further comprises a reduction gear mechanism. However, the present invention is not limited to the above-mentioned embodiments because the embodiments have been described for illustrative purposes. In the present invention, the planetary gear mechanism functions as a reduction gear mechanism, or functions to maintain a constant speed. Furthermore, the rotating direction of the cam unit is not fixed to a single direction. The wave shape of the cam guide may have one or more peaks and one or more troughs. The bellows may be formed of a variety of materials, such as metal or polymer, which can be easily deformed, has high pressure resistance and easily restores its original shape. Furthermore, a mechanical element, such as a bearing, may be provided between the cam guide and the cam guide engagement part to cause them to come into contact with each other without interference. Thus, the present invention provides a blood pump actuator which can convert rotating motion of a motor unit into rectilinear reciprocating motion using a cam unit, thereby expanding or contracting a bellows and increasing or reducing pressure of fluid, and providing pressure to pump blood out. Those skilled in the art will appreciate that various modifications, additions and substitutions are possible, without departing from the scope and spirit of the invention as disclosed in the accompanying claims.

The invention claimed is:

1. A blood pump actuator to generate a driving force for driving a blood pump, the blood pump actuator a motor unit having a stator and a rotor, and rotating to generate a rotating force;

a cam unit to convert the rotating motion of the motor unit into a rectilinear reciprocating motion, wherein the cam unit comprises a cylindrical cam which encircles the motor and rotates around the motor, said cylindrical cam having a cam surface which varies in axial position around the cylindrical cam; and a bellows unit comprising a bellows, which is expandable and contractible and contains a non-blood fluid therein, and an upper bellows plate and a lower bellows plate respectively attached to the upper and lower ends of the bellows and a lower bellows extension part extending below the lower bellows plate in a location outside the motor, wherein the lower bellows extension part and the lower bellows plate move upwards and downwards in a vertical direction according to the rectilinear reciprocating motion of the lower bellows extension part and the lower bellows plate;

the lower bellows extension part follows the cam surface of the cylindrical cam as the cam rotates around the motor; and the bellows repeatedly expands and contracts according to the vertical movement of the lower bellows plate, and provides a non-blood fluidic pressure output to drive the blood pump and the non-blood fluid causes blood in the blood pump to be pumped.

2. The blood pump actuator according to claim 1, wherein the cam unit comprises:

a cam having a cam guide continuously formed around an outer circumferential surface of a cylindrical body of the cam;

a cam cover mounted to an upper end of the cam; and a cam gear mounted to an end of the cam cover such that the cam gear is concentric with the cam and receives the rotating force of the motor unit.

3. The blood pump actuator according to claim 2, wherein the bellows unit is placed on the upper end of the cam unit, and the lower bellows plate comprises the lower bellows plate extension part, which extends at an edge of the lower bellows plate towards the cam unit, is perpendicular to the lower bellows plate, is spaced apart from the cam unit, and is placed outside the cam unit, wherein the lower bellows plate extension part comprises a cam guide engagement part provided on an inner surface thereof to engage with the cam guide.

4. The blood pump actuator according to claim 3, wherein the cam guide comprises a protruding cam guide, while the cam guide engagement part comprises a depressed cam guide engagement part.

5. The blood pump actuator according to claim 3, wherein the cam guide comprises a depressed cam guide, while the cam guide engagement part comprises a protruding cam guide engagement part.

6. The blood pump actuator according to claim 3, wherein the cam guide has a sine curve shape.

7. The blood pump actuator according to claim 3, wherein the cam guide has an asymmetrical curve shape.

8. The blood pump actuator according to claim 3, wherein the cam guide has a stepped shape.

9. The blood pump actuator according to claim 3, wherein the cam guide has a linear function curve shape having a peak and a trough.

10. The blood pump actuator according to claim 3, wherein the lower bellows plate extension part is continuously formed around an outer circumferential surface of the lower bellows plate.

11. The blood pump actuator according to claim 3, wherein the lower bellows plate extension part is discontinuously formed around an outer circumferential surface of the lower bellows plate.

12. The blood pump actuator according to claim 11, wherein the lower bellows plate comprises two or more discontinuous lower bellows plate extension parts which are arranged at respective positions dividing the lower bellows plate into even sectors.

13. The blood pump actuator according to claim 1, wherein the motor unit comprises a housing at a lower part thereof and is placed below the bellows unit, with a bellows guide extension part provided on an edge of the lower bellows plate and extending toward the cam unit, while the housing of the motor unit is provided with a bellows guide to guide the bellows guide extension part.

14. The blood pump actuator according to claim 13, wherein the bellows guide extension part comprises a rod-shaped part, while the bellows guide comprises a linear bushing to receive the bellows guide extension part therein.

15. The blood pump actuator according to claim 1, further comprising: a reduction gear mechanism placed between the motor unit and the cam unit.

16. The blood pump actuator according to claim 15, wherein the reduction gear mechanism comprises a planetary gear mechanism.

17. The blood pump actuator according to claim 16, wherein the planetary gear mechanism comprises: a sun gear having a gear part around an outer circumferential surface thereof a carrier placed at a predetermined height different from a height of the gear part of the sun gear; at least two or more planetary gears mounted on a surface of the carrier and engaging with the gear part of the sun gear; and a ring gear having a gear part around an inner circumferential surface thereof and engaging with the planetary gears, wherein the carrier is mounted to an inner surface of the rotor, the sun gear is concentric with the cam unit, and the ring gear is integrally formed with the cam gear.

18. The blood pump actuator according to claim 1, further comprising: a pressure regulating unit to regulate pressure in the bellows.

19. The blood pump actuator according to claim 18, wherein the pressure regulating unit comprises: a pressure gauge connected to the bellows through a pressure connection part and measuring pressure of the fluid in the bellows;

a fluid pump connected to the pressure connection part and supplying or discharging the fluid to or from the bellows;

control valves respectively placed between the bellows and the pressure gauge and between the pressure gauge and the fluid pump and controlling the flow of the fluid; and a pressure control unit to control both the control valves and the fluid pump in response to pressure in the bellows measured by the pressure gauge, thus maintaining inner pressure of the bellows within a predetermined pressure range.

20. A blood pump system, comprising: the blood pump actuator of claim 1; and a diaphragm which communicates with the bellows of the blood pump actuator through a connection part and is deformed according to changes in volume of the bellows, thus pumping blood from the blood pump system to a desired place in the body of a patient according to the deformation of the diaphragm.

* * * * *